United States Patent [19]

Wildman

[11] Patent Number: 4,909,735
[45] Date of Patent: Mar. 20, 1990

[54] STRAIGHT LINE ORTHODONTIC SETUP METHOD AND APPARATUS

[76] Inventor: Alexander J. Wildman, 2662 Donner Pl., Eugene, Oreg. 97401

[21] Appl. No.: 249,453

[22] Filed: Sep. 26, 1988

[51] Int. Cl.⁴ .............................................. A61C 3/00
[52] U.S. Cl. ........................................ 433/24; 433/53
[58] Field of Search ............................ 433/24, 53, 2, 3

[56] References Cited

U.S. PATENT DOCUMENTS

| | | | |
|---|---|---|---|
| 3,128,552 | 4/1964 | Broussard | 433/18 |
| 3,256,602 | 6/1966 | Broussard et al. | 433/13 |
| 3,439,421 | 4/1969 | Perkowski | 433/24 |
| 3,578,744 | 9/1969 | Wildman | 433/14 |
| 3,787,976 | 1/1974 | Cohen | 433/3 |
| 3,842,503 | 10/1974 | Wildman | 433/24 |
| 3,854,207 | 12/1974 | Wildman | 433/11 |
| 3,949,478 | 4/1976 | Schinhammer | 433/3 |
| 4,014,096 | 3/1977 | Dellinger | 433/3 |
| 4,097,993 | 7/1978 | Andrews | 433/20 |
| 4,360,341 | 11/1982 | Dellinger | 433/24 |
| 4,386,908 | 6/1983 | Kurz | 433/9 |
| 4,494,931 | 1/1985 | Wildman | 433/8 |
| 4,812,118 | 3/1989 | Creekmore | 433/24 |

*Primary Examiner*—Cary E. Stone
*Attorney, Agent, or Firm*—Marger & Johnson Inc.

[57] ABSTRACT

A method and apparatus for creating an orthodontic archform wherein the bracket archwire slots are level to one another. The method includes setting up separated model teeth in a straight line on a setup fixture to locate the brackets in a level position on the model teeth, transferring the model teeth and brackets to an alignment fixture, and positioning them in a curved arrangement defining an archform. An archwire can then be formed in the bracket slots either manually or by inserting and clamping the archwire in the slots and heat treating the archwire in an oven.

20 Claims, 5 Drawing Sheets

STRAIGHT LINE ORTHODONTIC SETUP METHOD AND APPARATUS

BACKGROUND OF THE INVENTION

This invention relates generally to orthodontic treatment and more particularly to a method of applying orthodontic brackets and archwires using an ideal set up.

In orthodontic treatment, teeth are moved by the spring force of an archwire engaged in brackets attached to teeth. The more accurately orthodontic brackets are positioned on the teeth, the less the archwire must be adjusted to produce the desired tooth movement.

The most common approach today is for the orthodontist to bond the brackets upon the teeth directly in the patient's mouth, using his experience to place the bracket in a free-hand manner. Sometimes the brackets are shaped so as to assist the orthodontist's eye in placing the brackets. Often the relationships between the archwire slots and the bases of the brackets are customized for the average tooth anatomy so that the slot remains as level as possible in all planes along the arch form, i.e to avoid having to form the arch wire with first, second and third order bends. This is called the straight wire technique by A Company, a division of Johnson & Johnson, which produces brackets as disclosed in Andrews U.S. Pat. No. 4,097,993.

Sometimes, plastic positionable guides representing the long axis of the tooth and a preconceived relationship of the bracket to the initial edge are inserted into the brackets as positional guides to aid in this free hand placement.

Another method of assuring positional accuracy is to place the bracket with a temporary fixation material (e.g. caramel) onto plaster models of the teeth so that the operator can view and adjust the bracket position out of the mouth. A transfer tray is then made to place the brackets in this relationship into the mouth. This is called the indirect bonding technique.

A number of attempts have been made to cut the teeth off the plaster models and to set them in wax in an ideal position, i.e. with the model teeth repositioned in an ideal arch form. In this process, the upper and lower model teeth are accurately articulated together according to the experience of the person setting the teeth. This is similar to the way plastic teeth are set up in preparation for making full dentures. The brackets are then placed on the teeth in a level position. This method is known as the ideal setup technique, of which a number of variations are known.

Archwires may then be made using the slots of the brackets as a guide. The problem that arises here is the difficulty of shaping archwires without disturbing the positions of the brackets that are temporarily attached to the model teeth. Either clumsy mechanical fixation is necessary or time-consuming care must be used not to dislodge the brackets from the teeth.

Some means must be provided to transfer the individual brackets back to the model of the present malocclusion of the patient's teeth so that indirect trays can then be made. An alternative method is to provide an accurate enough relationship between the bracket and the individual tooth so direct transfer could be made. Dellinger U.S. Pat. No. 4,360,341 discloses an individual tooth transfer fixture which encloses the bracket and tooth in a predetermined relationship. The combination of applying bonding material along with a burnished pad and index tabs is described in Wildman's U.S. Pat. No. 4,494,931.

One of the problems in this ideal set up arrangement is the lack of experienced operators to set up a large volume of cases. Another problem is the difficulty of communication between the lab technician and the orthodontist. Orthodontists do not wish to give up control of the placement of teeth to laboratory technicians. A third problem is the difficulty of designing a machine to place the brackets properly in a level position on the teeth when the arch form varies in each case in a curved manner. These drawbacks, and others mentioned above, particularly forming the arch wire, are exacerbated when shifting from labial to lingual orthodontics.

Accordingly, a need remains for a simpler, easier-to-use method for positioning orthodontic brackets in an ideal position and producing archwires with an ideal arch form.

SUMMARY OF THE INVENTION

It is, therefore, an object of the invention to simplify the ideal setup technique.

A second object is to simplify the setting up of model teeth in correct anatomical relationship to on another for an ideal setup of a patient's arch.

Another object is to make it easier to locate brackets on the model teeth in a level position, unencumbered by the arch form shape.

A further object is to utilize the bracket positions thus established, in combination with an ideal arch form, to form an archwire incorporating all dimensions of the ideal setup.

My invention is a method of creating an arch form with the bracket archwire slots level to one another. The basic approach is to separate the step of positional placement of the teeth for correct anatomical relationship to one another from the step of constructing the arch form. Most simply, this is done by setting up the separated model teeth initially in a straight line, preferably in slightly spaced apart position for ease of alignment, in correct mutual anatomic position; locate the brackets in a level position on the model teeth as positioned in a straight line; and transferring the model teeth and brackets as a group from the straight line arrangement to a curved arrangement defining an archform, which can be an ideal archform or variations thereof according to the particular patient and the operator's experience.

A further aspect of he invention is a method of creating a rugged replica of the exact position of the archwire slots in the brackets, positioned in a curved arrangement, so that an archwire can be formed in these slots either manually or by inserting and clamping archwires in the replica slots and heat treating the archwires in an oven. (Certain titanium nickel alloys when heated to the proper temperature and then cooled maintain whatever shape they are clamped in.)

The invention further includes a machine and fixtures therefor, or setup jig, to simplify the setting of teeth cut from a model, placement of the brackets, creation of an archform using the model teeth and forming of an arch wire.

The invention provides a technology which is more accurate than the straight wire method described by Andrews and simpler than the conventional ideal set up method. In this technique, the upper and lower archwires are made on setups that can be made ideal without being articulated one to another. This saves a large proportion of lab time and reduces the need of skilled technician's time.

The foregoing and other objects, features and advantages of the invention will become more readily apparent from the following detailed description of a preferred embodiment which proceeds with reference to the drawings.

DETAILED DESCRIPTION OF A PREFERRED EMBODIMENT

Straightline Setup Apparatus

Figure 1:
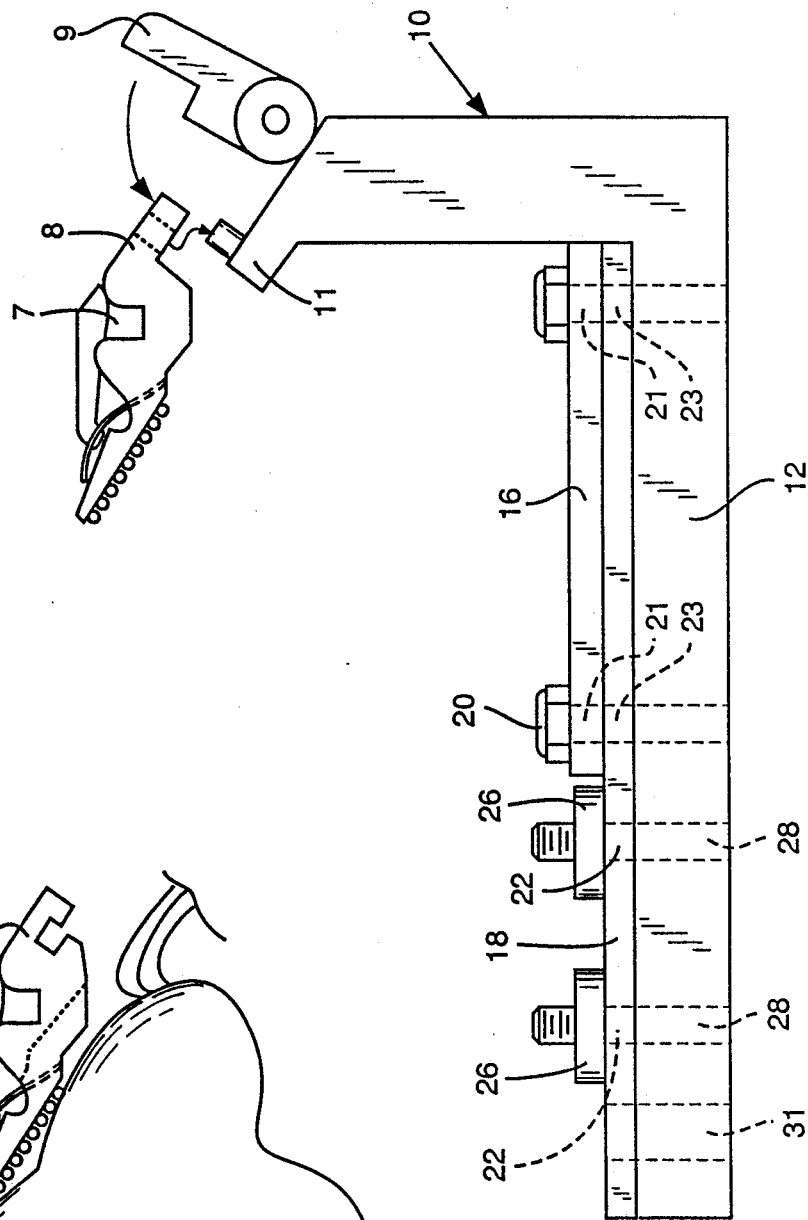
FIG. 1 is a side (mesiodistal) view of a model upper central incisor (shown inverted for clarity) having a prior art lingual bracket positioned on it using indexing tabs in accordance with the prior art.
Figure 2:
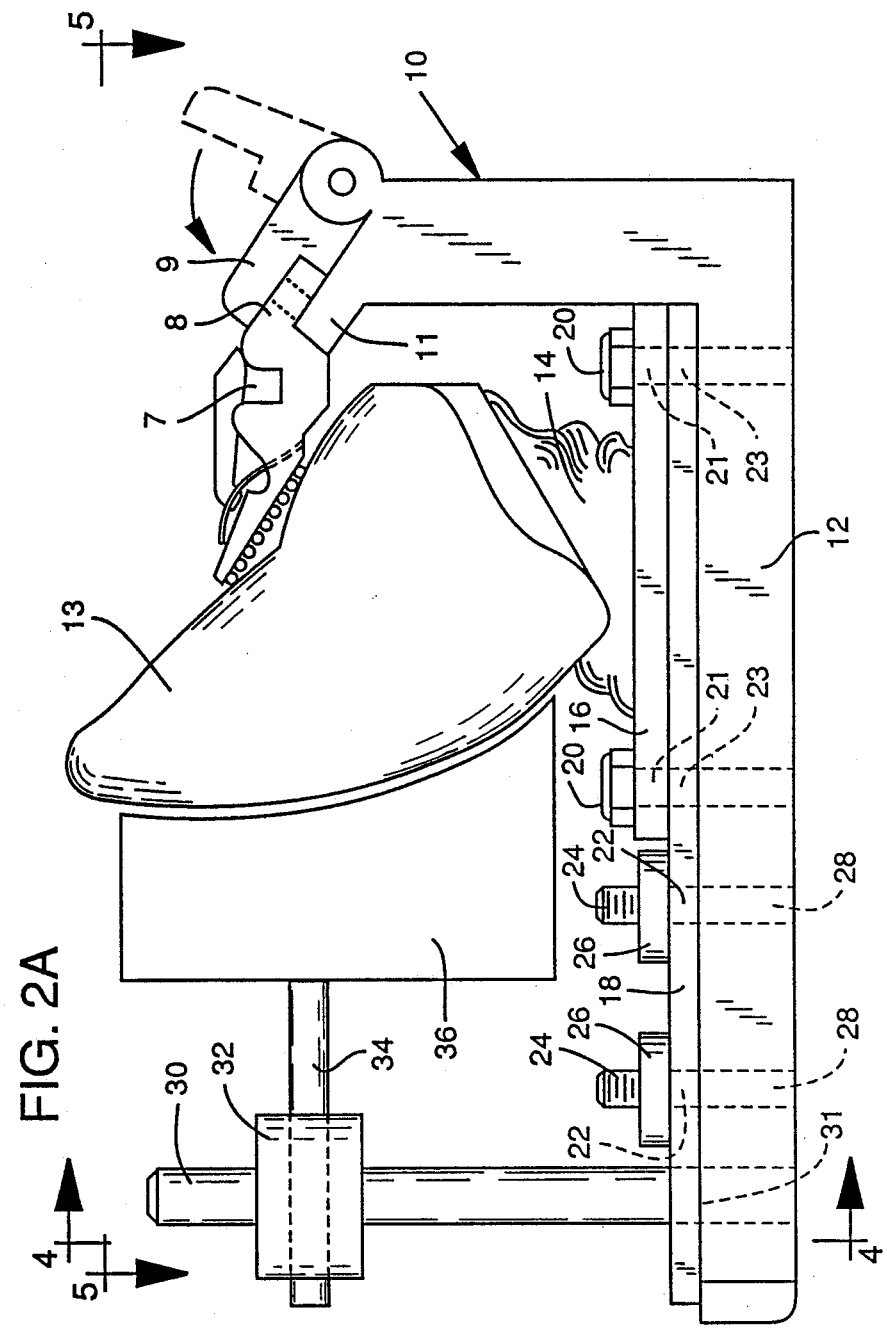
FIG. 2A is a view similar to FIG. 1 showing positioning of a lingual orthodontic bracket modified for positioning on a tooth using a straight line set up fixture in accordance with the method of the present invention.
FIG. 2B is a view similar to FIG. 2A showing operation of the clamping mechanism in the set up fixture.

FIG. 1 shows a model of an upper central incisor 4 having a lingual bracket 2 positioned on the lingual surface of the tooth. The bracket is retained in position by index tabs 6 as taught in U.S. Pat. No. 4,494,931.

Figure 6:
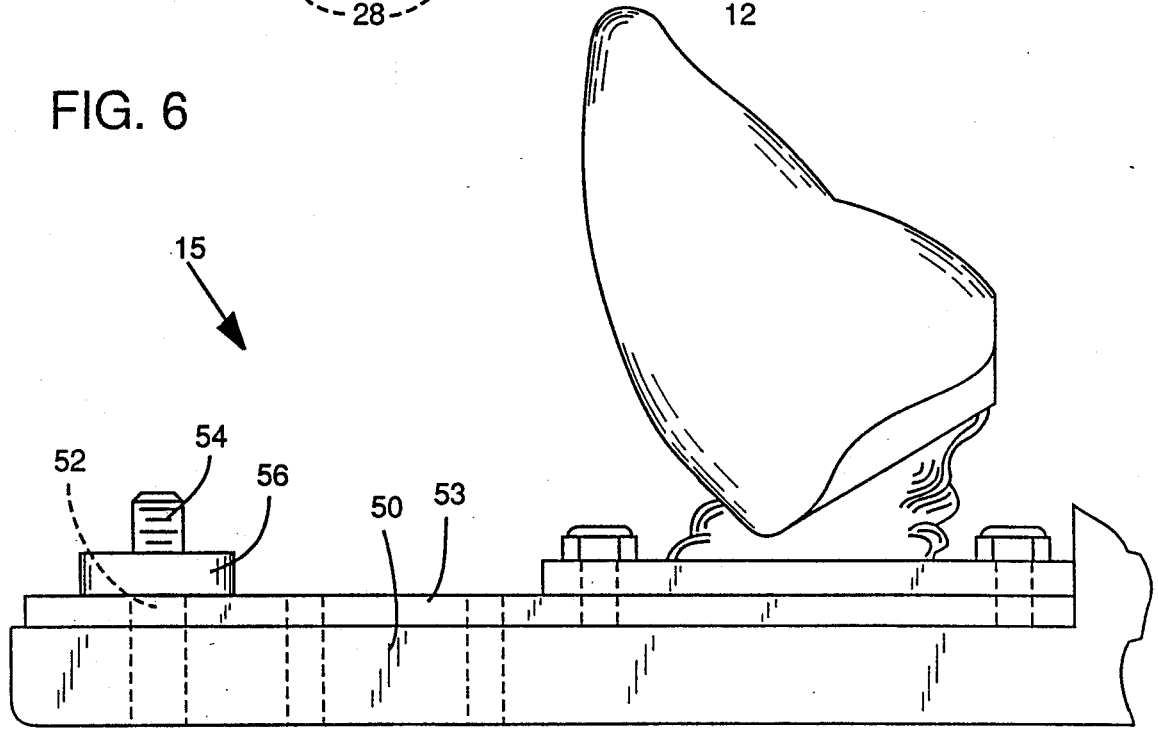
FIG. 6 is a view similar to FIG. 2A showing the model tooth mounted on the set up plate and intermediate plate and transferred tooth from the set up fixture to an alignment plate.
Figure 7:
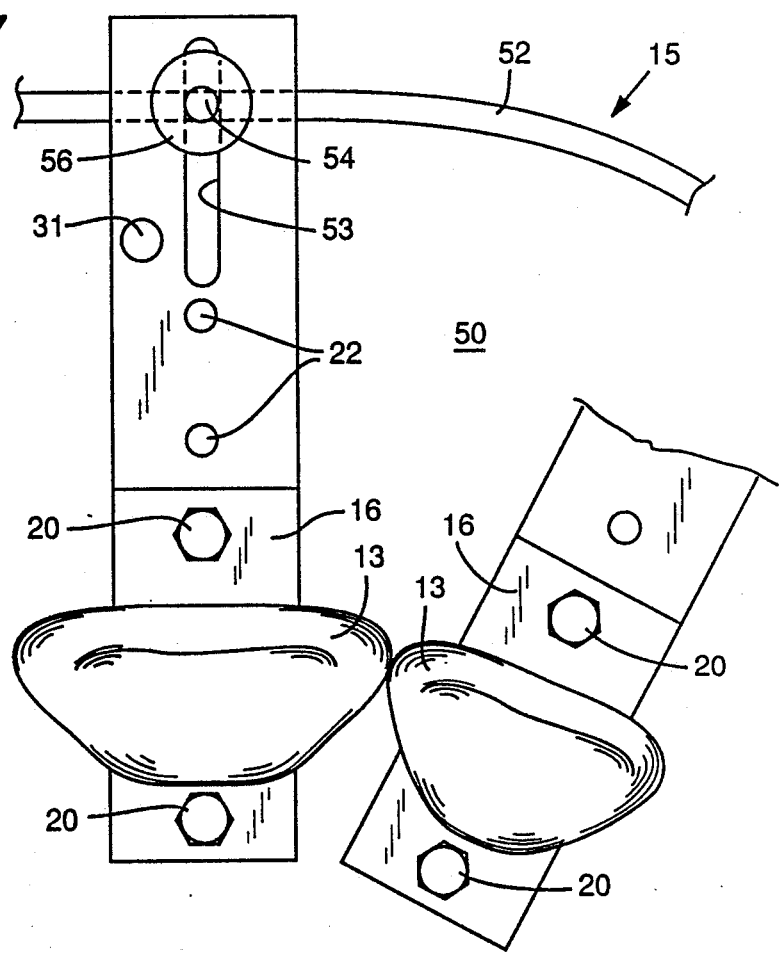
FIG. 7 is a top plan view taken along lines 7—7 in FIG. 6 showing two model teeth, each mounted on a respective set up plate and intermediate plate, both teeth in turn being arranged in an ideal arch form on the alignment plate of FIG. 6.
Figure 8:
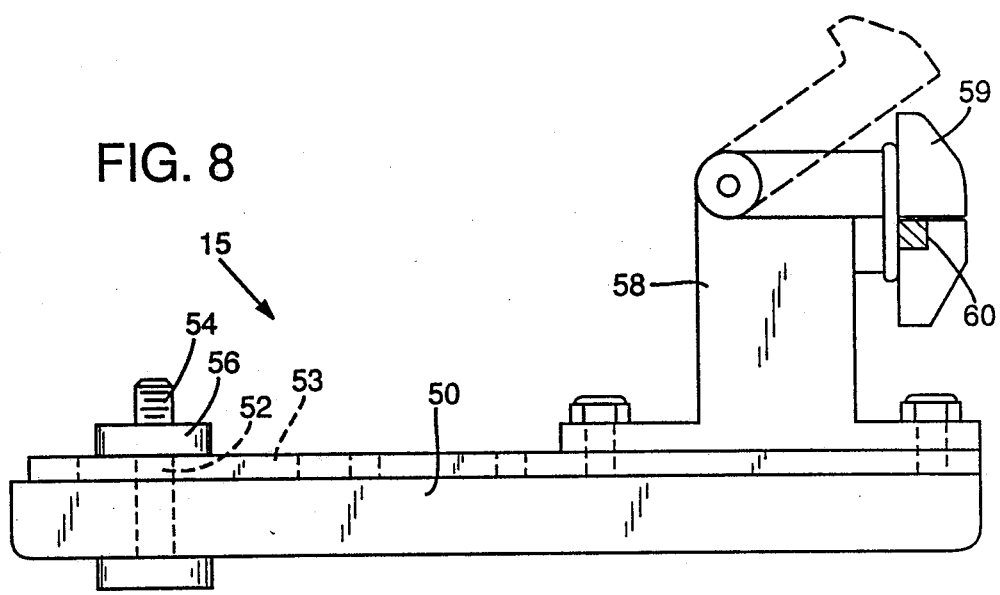
FIG. 8 is a view similar to FIG. 6 of the alignment plate and intermediate plate, after removal of the model tooth and set up plate, showing an archwire forming fixture in position for forming an archwire to conform to an ideal arch form according to the ideal arch set up created in FIG. 7.

Apparatus for straightline setup of plaster model teeth for positioning of orthodontic brackets and forming archwires to fit into archwire slots of the brackets, in accordance with the invention, generally comprises a straightline setup assembly 10, shown in FIGS. 2-5 and archwire forming assembly 15, shown in FIGS. 6-8.

Figure 3:
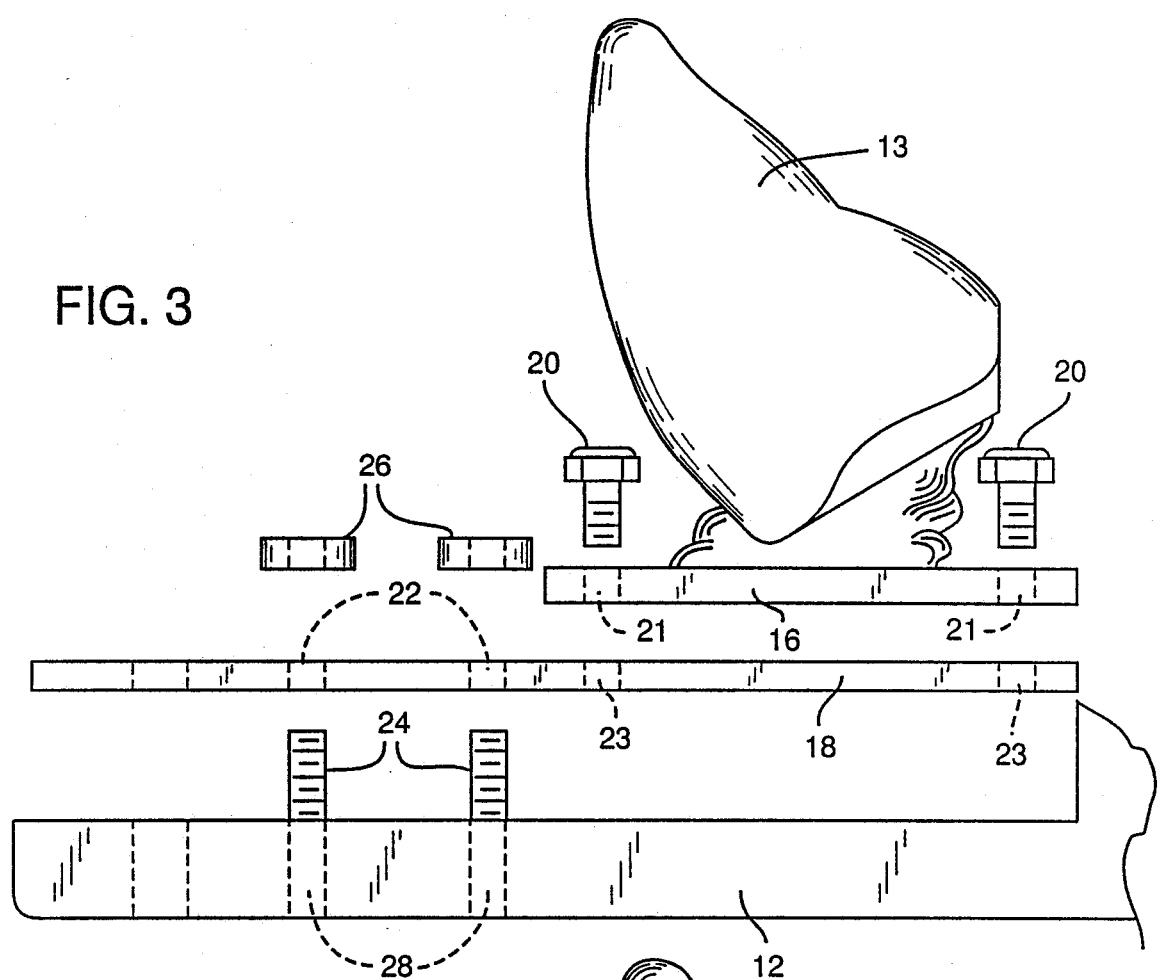
FIG. 3 is a view similar to FIGS. 2A and 2B showing an exploded view of the set up base plate, the intermediate base plate and the base of the set up fixture.

The straightline setup assembly 10 includes a setup fixture having a plurality of separate setup plate structures, each composed of a setup plate 16 and an intermediate plate 18, mounted as a group atop a base 12 The setup plate structures are positioned in a predetermined alignment relationship with one another and the base, preferably in a straight line, for mounting model teeth 13 on the setup plates 1 means of wax 14 in a straight line. As best seen in FIGS. 3 and 7, the setup plate is shorter than the intermediate plate. In the illustrated embodiment, the setup plates are detachably connected to the intermediate plates by bolts 20 in threaded holes 21, 23. The intermediate plates are, in turn detachably mounted on the base by bolts 24 in holes 22 and locked by nuts 26, bolts 24 are secured in holes 28 in base 12.

A plurality of bracket support fixtures 11 are positioned along one side of the base of fixture 12, preferably in a straight line and equidistantly spaced apart, to support a plurality of orthodontic brackets 8 with their archwire slots in a straight line. Each support fixture 11 is mounted adjacent one of the setup plates for aligning a corresponding model tooth 13 with each bracket.

The alignment assembly 15 includes an alignment plate 50 which is used for positioning the setup and intermediate plates 16, 18 bearing the model teeth in a curved arrangement defining an archform. A plurality of archwire forming fixtures 58, shown in FIG. 8, are used to form the archwire after the straightline set up is completed and transferred to the alignment plate to setup the desired archform. Each archwire forming fixture 58 is mountable on the intermediate plate when such is mounted on the alignment plate and the setup plate and model tooth is removed. Each forming fixture includes an archwire forming slot 60 positioned in the same relationship to the associated model tooth as the archwire slot 7 of the bracket 8 held in the bracket support fixture 11. Each fixture 58 is positioned on the alignment plate 50 in the position formerly occupied by one of the setup plates 16 and thereby assumes the same predetermined relationship to the model teeth in the archform arrangement as the bracket support fixture 11 in assembly 10.

In the illustrated embodiment, the intermediate plate is detachably mountable on the setup assembly base and the bracket support fixtures are fixedly mounted on the setup fixture base. This is not essential. Alternatively, the bracket support fixtures can be detachable from the assembly base fixture. It could, for example, be mounted atop a rearward extension of the intermediate plate. Other variations are also possible and may be useful.

Referring back to FIGS. 2A and 2B, the bracket support fixture protrudes upwardly from the base and includes a releasable clamp 9 for clamping a projection of the bracket. The bracket projection and clamp are designed with a complementary architecture, such as a hole in the bracket projection and pin in the clamp, for the clamp rigidly to engage the bracket.

Figure 4:
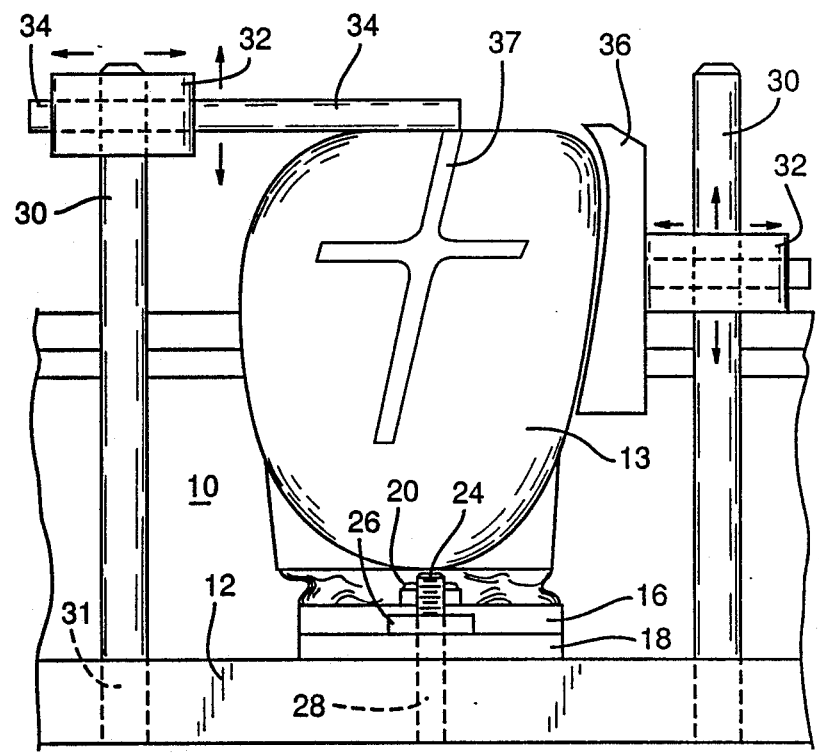
FIG. 4 is an elevational view taken along lines 4—4 in FIG. 2A showing relationship of the parts of the set up fixture to the labial side of the model tooth.
Figure 5:
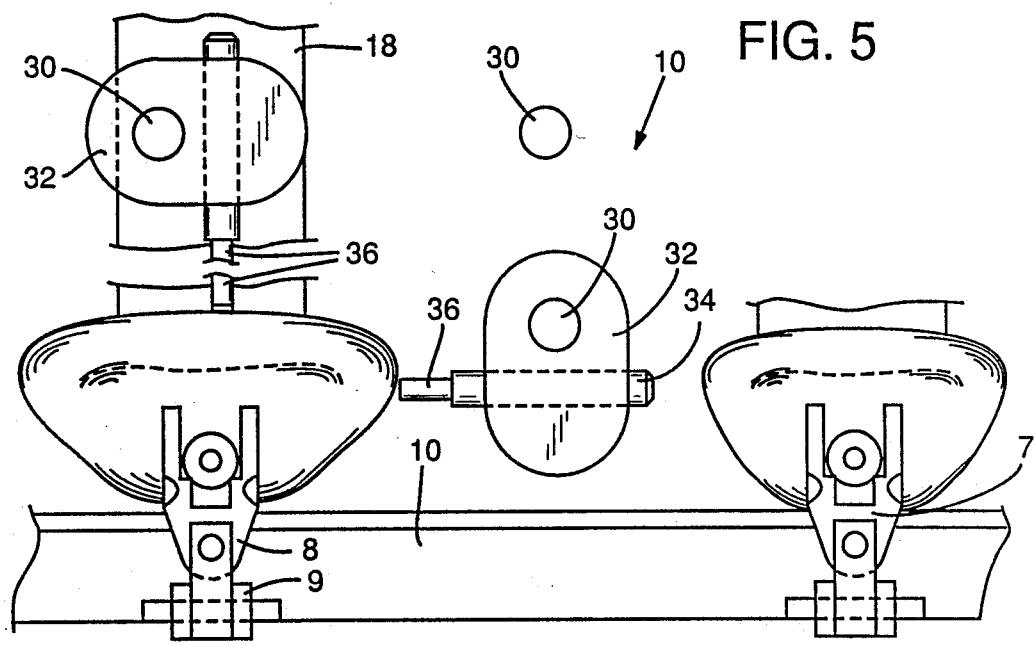
FIG. 5 is a top plan view taken along lines 5—5 in FIG. 2A.

The setup assembly 10 includes means for aligning each model tooth relative to its respective bracket support fixture in a labia-lingual direction, a mesiodistal direction, and in an inciso-gingival direction. A post 30 is mounted in a hole 31 in the base and intermediate plate forwardly (labially) adjacent each setup position, for supporting various forms of templates or gauges to aid in positioning the model tooth. FIGS. 2A and 5 show a template 36 supported by an arm 34 horizontally slidably inserted in a collar 32 received for slidable vertical movement on post 30 for positioning the model tooth labio-lingually, including controlling the tooth angle in that dimension. FIG. 4 shows a template 33 and a gauge 37 for controlling the position of the incisal edge of the tooth and the angulation of the long axis of the tooth in the mesio-distal dimension. Preferably, the stations for each tooth model are laterally spaced for ease of alignment by the operator.

As noted above, once the teeth are aligned in the straightline assembly, the intermediate and setup plates 16, 18 are detachable as a unit from the setup fixture base and transferred to the alignment fixture 50 to set up the desired archform. The alignment plate includes means for positioning and fixing the intermediate and setup plates as a unit in a generally radial pattern to define the curved archform relationship of the model teeth on a planar surface. As shown in FIGS. 7 and 8, this means can be provided by a radial slot 53 in the intermediate plate and a curved slot 52 in the alignment fixture. These slots permit radial and circumferential movement of the setup plate structures to enable the operator to position the model teeth collectively in a curved arrangement to define an archform. Means are provided, such as nuts 54 and bolts 56 inserted through the slots, for clamping each setup plate structure to the alignment plate once it is positioned.

Straightline Setup Method

Following is the procedure for setting up model teeth using the above-described assemblies:

1. Using wax to fix them in place, position model teeth cut from a plaster cast of a patient's mouth on the set up plates. These plates are mounted on the intermediate plates on the base of the fixture 10. Using the templates and gauges as needed, as well as the operators experience, the teeth are positioned in a straight line so that the cut off plaster teeth are positioned ideally in wax in relation to one another in a straight line. Preferably, the incisal edges are positioned in an ideal relation to one another incisogingivally and labially-lingually. The contact points of the teeth should also be in an ideal relation to one another and the long axes of the teeth should be in an ideal position one to another mesiodistally and labial lingually.

2. Align the model teeth, while retaining as closely as possible the foregoing straightline alignment, in contact or near contact with the bases of brackets held in a straight line so that the archwire slots are aligned in the same position mesiodistally, incisogingivally and labiolingually as closely as the unique anatomy of the teeth allows.

3. Remove each of the setup structures from the setup assembly by detaching the intermediate and setup plates, and teeth mounted thereon, as a unit, from the setup fixture base.

4. Position each tooth/plate complex on the alignment plate 50 in an ideal dental arch alignment, incorporating the desired curvature of an archform into the mutual position of the model teeth, and fix the intermediate plates to the alignment plate.

5. Remove the set up plate and the set up tooth by detaching the setup plate from each respective intermediate plate.

6. Position an archwire forming fixture 58 into the location from which each setup plate was removed to provide an archwire slot clamp 59 having an alignment between the forming fixture archwire slot and the intermediate plate determined by the alignment between the bracket archwire slot and the intermediate plate.

7. Form a ideal arch using the archwire slots in the forming fixture as a guide, either manually or, using titanium nickel archwire, by heat treating the arch wire as it is held in the forming fixture in an oven which will fix the titanium nickel archwires in the ideal position.

8. Position the brackets on the patient's teeth in a position replicating their anatomical position on the model teeth. This is done using the technique and indexing tabs disclosed in my above-referenced patent.

9. Install the archwire as formed above in the brackets as positioned on the patient's malocclusion.

Having illustrated and described the principles of my invention in a preferred embodiment thereof, it should be readily apparent to those skilled in the art that the invention can be modified in arrangement and detail without departing from such principles. Although described with reference to a lingual application, the techniques and apparatus can be readily applied to labial applications. I claim all modifications coming within the spirit and scope of the accompanying claims.

I claim:

1. A method of creating an orthodontic arch form with orthodontic bracket archwire slots level and aligned relative to one another in a horizontal plane, comprising:

making a model of a patient's malocclusion and separating individual model teeth from the model;

setting up the separated model teeth in a substantially straight line arrangement in a correct mutual anatomic position;

locating orthodontic brackets in a level position on the model teeth as positioned in said straight line;

memorizing the positions of the brackets on the model teeth;

transferring the model teeth as a group from the straight line arrangement to a curved arrangement defining an archform.

2. A method according to claim 1 including:

forming an archwire to conform to the archwire slots of the brackets in said curved arrangement;

mounting the brackets individually to the patient's teeth in positions replicating the memorized positions thereof on the corresponding model teeth; and installing the formed archwire in the brackets mounted on the patient's teeth.

3. A method according to claim 1 in which:

the step of locating the orthodontic brackets includes releasably mounting the brackets individually in bracket support fixtures and positioning the bracket support fixtures so that the brackets are arranged in a straight line; and the step of setting up the model teeth in a correct mutual anatomic position includes positioning the model teeth individually so that a surface of each model tooth approaches contact with a base of its respective bracket as closely as possible while retaining the correct mutual anatomic relationship of the model teeth in a straight line.

4. A method according to claim 3 including transferring the brackets individually to the patient's teeth in positions replicating the positions thereof on the corresponding model teeth and shimming the base of any bracket that could not be brought into contact with the surface of the model tooth in the setting-up step.

5. A method according to claim 3 in which:

the setting up step includes mounting the model teeth individually on separate setup plates and aligning the setup plates in a straight line in a predetermined relationship to the bracket support fixtures; and the step of transferring the model teeth from the straight line arrangement to a curved arrangement includes placing the setup plates on an alignment plate and locating the setup plates with the model teeth in a curved arrangement defining an archform.

6. A method according to claim 5 including;

mounting a plurality of archwire forming fixtures on the alignment plate with each archwire forming fixture positioned in a relationship to each setup plate which corresponds to the predetermined relationship of the setup plate to the respective bracket support fixture in the setting up step; and forming an archwire in the archwire fixtures.

7. A method according to claim 1 including positioning a plurality of archwire forming fixtures, each having an archwire slot, relative to the model teeth in said curved arrangement defining an archform, so that the positions of the archwire slots of the fixtures replicate the positions of the archwire slots in the brackets relative to the respective model teeth established in the straight line arrangement.

8. A method according to claim 1 in which:

the setting up step includes:

mounting the model teeth individually on separate setup plates;

aligning the setup plates in a predetermined labio-lingual index position relative to one another; and positioning the model teeth in a mutually correct anatomical position in a straight line on the setup plates; and the transferring step includes transferring the model teeth on the setup plates on a plane into said curved arrangement while retaining the position of the teeth in relation to the index position, thereby transforming the index positions of the setup plates to said curved arrangement.

9. A method according to claim 8 including positioning a plurality of archwire forming fixtures, each having an archwire slot, relative to the index positions of the setup plates in said curved arrangement defining an archform, whereby the positions of the archwire slots of the fixtures replicate the positions of the archwire slots in the brackets relative to the respective model teeth established in the straight line arrangement, and forming an archwire using the archwire slots in the fixture.

10. Apparatus for straightline setup of plaster model teeth for positioning of orthodontic brackets and forming archwires to fit into archwire slots of the brackets, the apparatus comprising;

a plurality of separate setup plates structure mounted as a group atop a setup fixture in a predetermined alignment relationship for mounting model teeth thereon on a straight line; and a plurality of bracket support fixtures positioned to support a plurality of orthodontic brackets with their archwire slots in a straight line, each support fixture being mounted adjacent one of the setup plates for aligning a corresponding model tooth with each bracket.

11. Apparatus according to claim 10, in which the setup plate structures are detachable from the setup fixture, further including:

an alignment fixture for positioning the setup plate structures thereon with the model teeth in a curved arrangement defining an archform; and a plurality of archwire forming fixtures, each forming fixture being mountable on an alignment plate in a predetermined relationship to one of the setup plates;

each forming fixture including an archwire forming slot positioned in the same position to the associated model as the archwire slot of the bracket held in the bracket support fixture.

12. Apparatus according to claim 11 in which the setup plate structures includes an intermediate plate detachably mountable on the setup fixture and the bracket support fixtures which are fixedly mounted on the setup fixture.

13. Apparatus according to claim 11 in which the bracket support fixtures are detachably mounted on the setup fixture.

14. In combination, apparatus according to claim 10 and an orthodontic bracket, including a releasable clamp in the bracket support fixture and complementary architecture in the bracket for the clamp to rigidly engage the bracket.

15. Apparatus according to claim 10, including means for aligning each model tooth relative to its respective bracket support fixture in a labio-lingual direction.

16. Apparatus according to claim 10, including means for aligning each model tooth relative to its respective bracket support fixture in a mesio-distal direction.

17. Apparatus according to claim 10, including means for aligning each model tooth relative to its respective bracket support fixture in an inciso-gingival direction.

18. Apparatus according to claim 10, in which the setup plate structures are detachable from the setup fixture, further including:

an alignment fixture for positioning the setup plates thereon with the model teeth in a curved arrangement defining an archform; and a plurality of archwire forming fixtures, each forming fixture being mountable on an alignment plate in a predetermined relationship to one of the setup plate structures and including means for holding an arch wire for forming same;

the alignment plate including means for positioning and fixing the setup plate structures in a generally radial pattern to define the curved archform relationship of the model teeth.

19. Apparatus according to claim 18, in which the positioning and fixing means includes a radial slot in the setup plate structures and a curved slot in the alignment fixture, to permit radial and circumferential movement of the setup plate structures and means for clamping each setup plate structure and the alignment fixture together.

20. Apparatus according to claim 18 in which each setup plate structure includes a setup plate detachably mounted atop an intermediate plate and the combined setup and intermediate plates being detachably mountable on the setup fixture in a predetermined position.

* * * * *

UNITED STATES PATENT AND TRADEMARK OFFICE
CERTIFICATE OF CORRECTION

PATENT NO.  : 4,909,735
DATED       : March 20, 1990
INVENTOR(S) : Alexander J. Wildman It is certified that error appears in the above-identified patent and that said Letters Patent is hereby corrected as shown below:

Column 1, line 32, change "initial" to --incisal--;

Column 3, line 66, change "plates 1 means" to --plates 16 by means--;

Column 4, line 51, change "labia-lingual" to --labio-lingual--;

Column 7, line 48, change "plates structure" to --plate structures--;

line 56, change "plates for" to --plate structures for--; change "tooth-" to --tooth--.

Signed and Sealed this

Third Day of September, 1991

Attest:

HARRY F. MANBECK, JR.

*Attesting Officer*     *Commissioner of Patents and Trademarks*